US012796915B2

(12) United States Patent
Sinha et al.

(10) Patent No.: US 12,796,915 B2
(45) Date of Patent: Nov. 17, 2026

(54) MAPPING OF CORNEAL TOPOGRAPHY USING A VR DEVICE

(71) Applicant: Verily Health Inc., Dallas, TX (US)

(72) Inventors: Supriyo Sinha, Menlo Park, CA (US); Jeremy Chan, San Jose, CA (US); Dimitri Azar, Chicago, IL (US); Xingting Gong, San Jose, CA (US)

(73) Assignee: Verily Health Inc., Dallas, TX (US)

( * ) Notice: Subject to any disclaimer, the term of this patent is extended or adjusted under 35 U.S.C. 154(b) by 735 days.

(21) Appl. No.: 18/304,758

(22) Filed: Apr. 21, 2023

(65) Prior Publication Data

US 2023/0337910 A1 Oct. 26, 2023

Related U.S. Application Data

(60) Provisional application No. 63/334,517, filed on Apr. 25, 2022.

(51) Int. Cl.
*A61B 3/113* (2006.01)
*A61B 3/107* (2006.01)
*A61B 3/00* (2006.01)

(52) U.S. Cl.
CPC .............. *A61B 3/113* (2013.01); *A61B 3/107* (2013.01); *A61B 3/0008* (2013.01)

(58) Field of Classification Search
CPC ........ A61B 3/0008; A61B 3/107; A61B 3/113
See application file for complete search history.

(56) References Cited

U.S. PATENT DOCUMENTS 9,361,519 B2 * 6/2016 Horesh .................... A61B 3/14
9,480,396 B2 * 11/2016 Takii .................... A61B 3/1005
9,615,739 B2 * 4/2017 Farrer .................... A61B 3/107
2014/0243623 A1 * 8/2014 Kersting ................ A61B 3/107 600/301
2015/0173610 A1 * 6/2015 Marcos Munoz ... A61B 3/0008 351/246
2016/0026863 A1 * 1/2016 Hakoshima ............ A61B 3/113 382/103
2017/0123526 A1 5/2017 Trail et al.
2017/0293794 A1 * 10/2017 Tsurumi .................. A61B 3/11
(Continued)

OTHER PUBLICATIONS

"Corneal surface reconstruction algorithm that uses Zernike polynomial representation," Sicam et al., J. Opt. Soc. Am. A/vol. 21, No. 7/Jul. 2004, pp. 1300-1306.
(Continued)

*Primary Examiner* — Nicholas R. Pasko
(74) *Attorney, Agent, or Firm* — Christensen O'Connor Johnson Kindness PLLC

(57) ABSTRACT

A method for performing corneal topography. Image data produced by an eye tracker camera that is integrated into an eye tracking virtual reality headset is processed, to detect eye position and movement during ophthalmic examination of the wearer of the headset. The image data produced by the eye tracker camera is also processed to detect a spacing of spots within, or a shape of, a Purkinje image that is in the image data. A topography map of the wearer's cornea is produced based on the detected spacing or the detected shape of the Purkinje image and based on the detected eye position and movement. Other aspects are also described and claimed.

18 Claims, 3 Drawing Sheets

(56) References Cited

U.S. PATENT DOCUMENTS

| | | | | |
|---|---|---|---|---|
| 2018/0125355 | A1* | 5/2018 | Mrochen | A61B 3/0025 |
| 2019/0042842 | A1* | 2/2019 | Cavin | G06V 40/197 |
| 2021/0093193 | A1* | 4/2021 | Birkner | A61B 3/101 |
| 2021/0212601 | A1* | 7/2021 | Neal | A61B 3/028 |

OTHER PUBLICATIONS

"Curvature of Surfaces in 3-Space," Michael Garman and Jessica Bonnie, https://blogs.goucher.edu/verge/files/2016/01/Curvature_of_pdf published Jan. 1, 2016, Goucher College, pp. 1-13.

"Reconstructing ocular surfaces by Purkinje images: an exact ray approach," Jason Turuwhenua, Bioengineering Institute, University of Auckland, Private Bag 92019, Auckland 1142, New Zealand, Ophthal. Physiol. Opt. 2009 29, pp. 80-91.

"Determination of the radius of curvature of the anterior lens surface from the Purkinje images," George Smith and Leon F. Garner, Ophthal. Physiol. Opt. vol. 16. No. 2, pp. 135-143, 1996.

International Search Report and Written Opinion received for PCT Patent Application No. PCT/US2023/019493, mailed on Jun. 9, 2023, 10 pages.

* cited by examiner

MAPPING OF CORNEAL TOPOGRAPHY USING A VR DEVICE

CROSS-REFERENCE TO RELATED APPLICATION

This application claims the benefit of U.S. Provisional Application No. 63/334,517, filed on Apr. 25, 2022.

FIELD

The subject matter of this disclosure relates to techniques for measuring the surface of the cornea of a human user, using a virtual reality, VR, headset worn by the user.

BACKGROUND

It is often desirable to map the surface of the cornea to determine its topography for monitoring scarring, astigmatism, or keratoconus, or for other reasons. However, using a typical corneal topographer can be time consuming and some eye care professionals do not have such a machine in their office.

SUMMARY

An aspect of the disclosure here is a method for producing a topography map of the cornea of a user (showing details of the curved surface of the cornea) while the user is wearing a VR headset that is also being used simultaneously to test one or more other eye conditions of the user (e.g., visual acuity, visual field, contrast sensitivity, etc.) The VR headset contains an eye tracker camera, which may be one that images in the near infrared, NIR, region of light. A NIR illumination source may be integrated in the headset and is configured to illuminate the eye of the user (wearer of the headset) with a NIR light pattern which is not just a single, circular spot. Reflections of this light pattern from the structure of the eye are referred to as Purkinje images, and one or more of these are captured within the digital images that are produced by the eye tracker camera. The eye tracker camera is dual purposed: eye tracking software (that may be executed by a processor, for example one that is in the VR headset) processes the digital images produced by the camera to measure position and movement of the wearer's eye; corneal topography software processes the digital images to detect a spacing of spots within, or the shape of, a Purkinje image, which spacing or shape varies according to the topography of the cornea. As the eye moves (or changes its position), the processor tracks the eye movement and time-aligns it with the detected changes in the spacing or shape of the Purkinje image. This is also referred to here as synchronizing the detected changes in spacing or shape of the Purkinje image with the detected positions of the eye. The detected position of the eye may be changing due to the user looking at different stimuli of other ophthalmic examinations. In this manner, it is possible to produce a topographic map of the entire surface of the cornea using only a sparse light pattern while the eye is moving naturally through a wide range of angles by virtue of one or more other ophthalmic examinations that are taking place simultaneously. As a result, there is no need to separately instruct the user (to for example gaze at different directions) for performing the corneal topography.

In another aspect, a programmed processor receives detected eye position and detected eye movement of an eye during ophthalmic examination of a person, processes mage data for the eye to detect a spacing of spots within, or a shape of, a Purkinje image that is in the image data, and produces a topography map of the person's cornea based on the detected spacing or the detected shape of the Purkinje image and based on the detected eye position and movement.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have advantages not specifically recited in the above summary.

BRIEF DESCRIPTION OF THE DRAWINGS

Several aspects of the disclosure here are illustrated by way of example and not by way of limitation in the figures of the accompanying drawings, in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
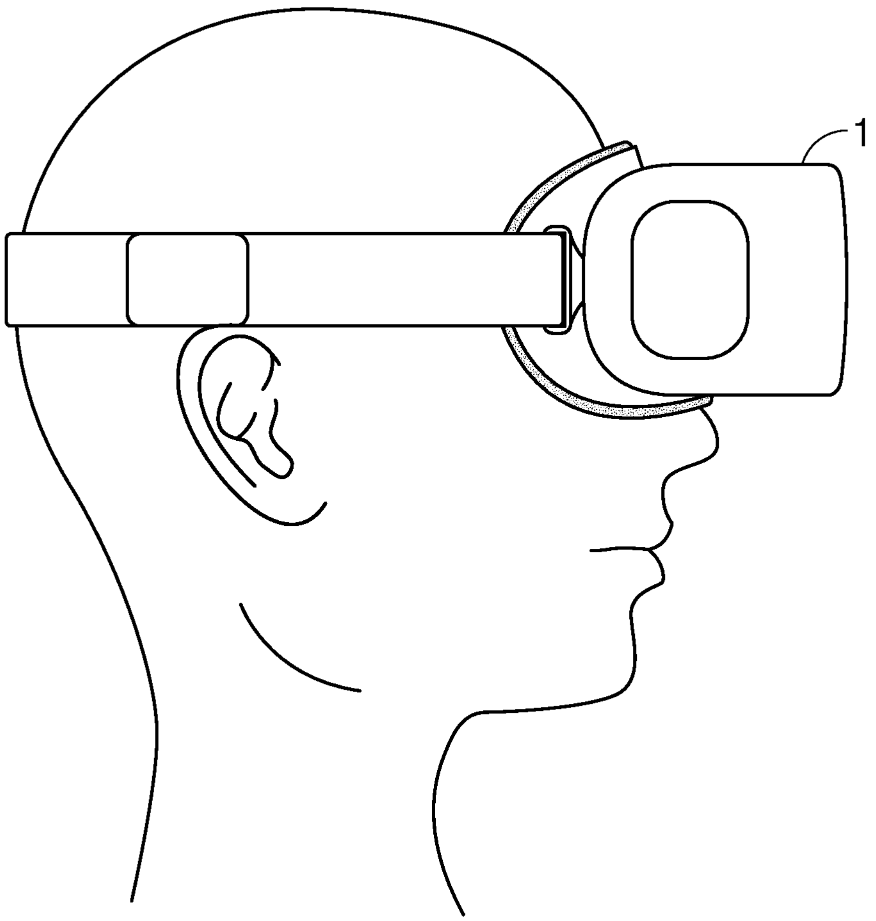
FIG. 1 depicts a user wearing a VR headset.
Figure 2:
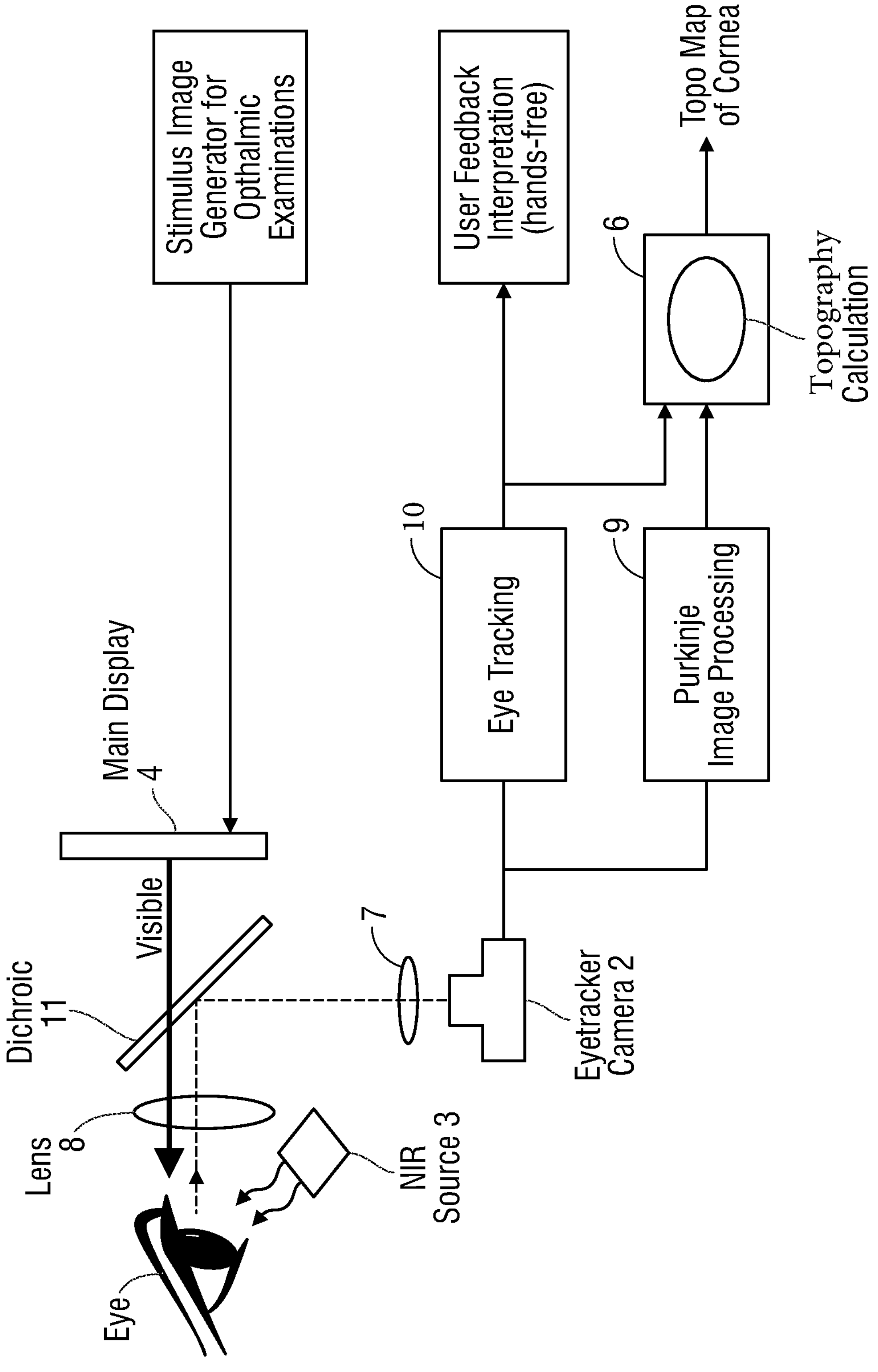
FIG. 2 is a block diagram of an example system having a VR headset that is used to perform corneal topography.

FIG. 1 depicts a user wearing a VR headset 1 as part of a system that performs various ophthalmic examinations on the eyes of the wearer, such as eye motility, visual acuity, visual field, contrast sensitivity, etc. FIG. 2 is a block diagram of an example of such a system that can also perform corneal topography upon an eye of the wearer. Note that certain blocks shown in FIG. 2 also support the operations of a method performed by a programmed processor for corneal topography.

Referring to FIG. 2, the VR headset 1 has integrated therein a dichroic filter 11 that is angled relative to a path taken by a visible light image that is emitted from a display 4. This visible light image passes through the first dichroic filter 11 and a lens 8 before forming visible images when it impinges on the eye, so that the wearer can see what is being presented on the display 4. The display 4 may be a main display of the headset, which serves to present high resolution virtual reality images to the eye.

Figure 3:
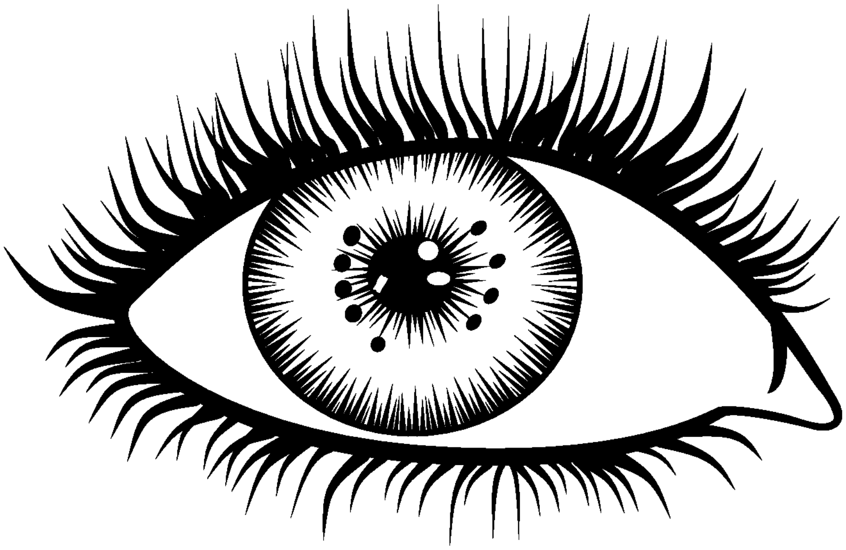
FIG. 3 shows an example near infrared light pattern suitable for performing corneal topography, which is illuminating an eye of the wearer of the headset.

The VR headset 1 being an eye tracking headset also has integrated therein an eye tracker camera 2, and a near infrared, NIR, illumination source 3 that produces a NIR light pattern on the eye of the wearer of the headset. The NIR illumination source 3 may include an array of NIR light emitting diodes, LEDs, which produces a light pattern being an array of two or more spots, such as in the example shown in FIG. 3. Alternatively, the light pattern may be, or may include a curved or angular band. The NIR light pattern that impinges on the eye results in reflections that in turn may pass through the lens 8 before being reflected off the first dichroic filter 11. Those reflections by virtue of the dichroic filter 11 being angled become directed towards an imaging lens 7 of the eye tracker camera 2. The eye tracker camera 2 is an imaging device whose image data is processed by eye tracking software that may be executed by a processor, to detect eye position and eye movement of the wearer of the headset, and that tracks the direction of wearer's gaze in real-time. These functions are performed by a programmed processor (e.g., one or more microelectronic processors that are executing instructions stored in a machine-readable medium such as solid state memory that may be part of an article of manufacture), depicted as a block labeled eye tracking 10. The programmed processor may also perform additional tasks described below such as Purkinje image processing 9, topography calculation 6, and user feedback interpretation. The processor may be one that is integrated within the headset, or it may be one that is external to the headset that is receiving the image data being produced by the eye tracker camera 2 as an incoming data stream. With the addition of digital processing capability referred to here as user feedback interpretation logic that processes the tracked direction of gaze produced by the eye tracking 10 and the image data produced by the eye tracker camera 2, the system enables handsfree feedback from the wearer of the headset during the ophthalmic examinations. This enables the wearer of the VR headset 1 to for example select amongst several testing options by "clicking" with one or more of their eyes, which selections are detected by the user feedback interpretation logic.

The eye tracker camera 2 is dual purposed here: the processor is not only configured to process the image data produced by the eye tracker camera 2 to perform eye tracking 10 (to detect eye position and eye movement of the wearer of the headset), but it also processes the image data to detect a spacing of spots within, or a shape of, a Purkinje image that is in the image data. The latter function is depicted as a block labeled Purkinje image processing 9. As above, the processor that does the Purkinje image processing 9 may be one that is integrated within the headset, or it may be one that is external to the headset and is receiving the image data being produced by the eye tracker camera 2 as an incoming data stream. The processor is further configured to produce a topography map of the wearer's cornea, based on the detected spacing or the detected shape of the Purkinje image and based on the detected eye position and eye movement—this function is depicted in the figure as topography calculation 6.

The topography calculation 6 may be motivated based on the following understanding. For a given NIR illumination source and distance from eye to the display 4 (which may be assumed constants for all users), a change in gaze will shift the NIR reflections, and hence the Purkinje images. The nature of these detected shifts should vary based on cornea shape, so plotting these shifts vs. gaze curves should empirically reveal something about corneal topography. For example, a strongly conically shaped eye (of a patient suffering from keratoconus) might have exceptionally large shifts in Purkinje images with gaze, while a less-curved cornea might have smaller shifts. Of course, each Purkinje image itself (associated with a fixed gaze) should also depend on cornea shape, but studying an individual Purkinje image would provide less signal to noise as compared to scanning many gaze angles.

More specifically, the topography calculation 6 produces the topography map, for example by: tracking movement of the eye (e.g., as stream or sequence of eye positions or gaze, over time), and time-aligning the tracked eye movement with the detected changes in the spacing or shape or position of the Purkinje image (e.g., as a stream or sequence of such changes over time.) In other words, the processor may assign each detected change in the Purkinje image to a corresponding, detected gaze. The way the Purkinje image changes is a function of the cornea topography, and so the detected (or computed) changes in the Purkinje image will inform the cornea topography. As the gaze changes (and is tracked), the corresponding detected change in the Purkinje image is recorded to produce a topography map covering the entire surface of the cornea.

In one aspect, the processor determines a point or location on the cornea, and/or computes the curvature at the point or location on the cornea, based on having detected a change in the Purkinje image and based on the detected eye position or gaze at the time of the detected change in for example the spacing or shape or position of the Purkinje image. These operations are then repeated for several locations on the cornea, to produce the topography map covering the entire surface of the cornea.

This wide coverage of the cornea may be achieved even though a sparse light pattern was used to illuminate the eye, because the eye is moving across a wide range by virtue of one or more other ophthalmic examinations that are taking place, e.g., during eye motility testing. In addition, since the detected eye position and the detected eye movement are taking place while the eye of the wearer is moving "naturally" for other purposes, there is no need to separately instruct the user (to for example gaze at different directions) for performing the corneal topography.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting.

What is claimed is:

1. A system for performing corneal topography, the system comprising:

a device including an eye tracker camera and a near infrared (NIR) illumination source adapted to produce a NIR light pattern on an eye of a user of the device; and a processor coupled to memory storing instructions that when executed by the processor cause the system to perform operations including:

i) processing image data produced by the eye tracker camera to detect eye position and eye movement of the user;

ii) processing the image data produced by the eye tracker camera to detect at least one of a spacing of spots within a Purkinje image of the image data, a shape of the Purkinje image, or a position of the Purkinje image within the image data; and iii) producing a topography map of a cornea of the user by:

tracking the eye movement as the eye moves between a plurality of positions;

indexing, for a plurality of locations on the cornea each corresponding to one of the positions:

at least one of the spacing of the spots within the Purkinje image or the shape of the Purkinje image; and the position of the Purkinje image within the image data produced by the eye tracker camera; and generating the topography map by determining a curvature of the cornea at each of the locations based on the indexed spacing of the spots, shape, or position of the Purkinje image at each of the locations.

2. The system of claim 1 wherein the illumination source comprises an array of NIR light emitting diodes, LEDs, and the light pattern is an array of spots.

3. The system of claim 1 wherein the operations further comprise executing one or more other ophthalmic examinations while acquiring the image data for producing the topography map to induce the eye position and the eye movement, which are detected for producing the topography map of the user's cornea.

4. The system of claim 1 wherein producing the topography map comprises:

time-aligning the tracked eye movement with the detected changes in the spacing or shape of the Purkinje image.

5. The system of claim 4 wherein producing the topography map further comprises:

determining a point on the cornea, based on the detected eye position at the time of a given detected change in the spacing or shape of the Purkinje image; and computing a curvature at said point based on the given detected change.

6. A method for performing corneal topography, the method comprising:

processing image data produced by an eye tracker camera that is integrated into an eye tracking virtual reality device, to detect eye position and movement during an ophthalmic examination of a user of the eye tracking virtual reality device;

processing the image data produced by the eye tracker camera to detect at least one of a spacing of spots within a Purkinje image of the image data, a shape of the Purkinje image, or a position of the Purkinje image within the image data; and producing a topography map of a cornea of the user by:

tracking the eye movement as the eye moves between a plurality of positions;

indexing, for a plurality of locations on the cornea each corresponding to one of the positions:

at least one of the spacing of the spots within the Purkinje image or the shape of the Purkinje image; and the position of the Purkinje image within the image data produced by the eye tracker camera; and generating the topography map by determining a curvature of the cornea at each of the locations based on the indexed spacing of the spots, shape, or position of the Purkinje image at each of the locations.

7. The method of claim 6 wherein producing the topography map comprises tracking movement of the eye, and time-aligning the tracked eye movement with detected changes in the spacing or shape of the Purkinje image.

8. The method of claim 6 wherein producing the topography map comprises:

a) determining a point on the cornea, based on the detected eye position at the time of a given detected change in the spacing or shape of the Purkinje image;

b) computing curvature at said point based on the given detected change; and repeating a)-b) for a plurality of points on the cornea to produce the topography map for an entire surface of the cornea.

9. The method of claim 6 wherein the Purkinje image is a result of a NIR light pattern impinging on and reflecting off the eye of the user and comprises a plurality of spots.

10. The method of claim 9 wherein producing the topography map comprises tracking movement of the eye, and time-aligning the tracked eye movement with detected changes in the spacing or shape of the Purkinje image.

11. The method of claim 10 wherein producing the topography map comprises:

a) determining a point on the cornea, based on the detected eye position at a time of a given detected change in the spacing or shape of the Purkinje image;

b) computing curvature at said point based on the given detected change; and repeating a)-b) for a plurality of points on the cornea to produce the topography map for an entire surface of the cornea.

12. The method of claim 11 further comprising: executing one or more other ophthalmic examinations contemporaneously with acquiring the image data for producing the topography map to induce the eye position and the eye movement, which are detected for producing the topography map of the cornea.

13. An article of manufacture comprising a non-transitory machine-readable medium having stored therein instructions that when executed by a processor:

acquire image data of an eye of a person with an eye tracker camera;

detect eye position and eye movement of the eye during ophthalmic examination of the person based on the image data;

process the image data for the eye to detect at least one of a spacing of spots within a Purkinje image of the image data, a shape of the Purkinje image, or a position of the Purkinje image within the image data; and produce a topography map of the person's cornea by:

tracking the eye movement as the eye moves between a plurality of positions;

indexing, for a plurality of locations on the cornea each corresponding to one of the positions:

at least one of the spacing of the spots within the Purkinje image or the shape of the Purkinje image; and the position of the Purkinje image within the image data; and generating the topography map by determining a curvature of the cornea at each of the locations based on the indexed spacing of the spots, shape, or position of the Purkinje image at each of the locations.

14. The article of manufacture of claim 13 wherein the non-transitory machine-readable medium has stored therein instructions that, when executed by the processor, produce the topography map by time-aligning the tracked eye movement with the detected changes in the spacing or shape of the Purkinje image.

15. The article of manufacture of claim 13 wherein the non-transitory machine-readable medium has stored therein instructions that when executed by the processor produce the topography map by:

a) determining a point on the cornea, based on the detected eye position at the time of a given detected change in the spacing or shape of the Purkinje image;

b) computing curvature at said point based on the given detected change; and repeating a)-b) for a plurality of points on the cornea to produce the topography map for an entire surface of the cornea.

16. The article of manufacture of claim 13 wherein the non-transitory machine-readable medium has stored therein instructions that, when executed by the processor execute one or more other ophthalmic examinations contemporaneously while acquiring the image data for producing the topography map to induce the eye position and the eye movement, which are detected for producing the topography map of the cornea.

17. The article of manufacture of claim 16 wherein the non-transitory machine-readable medium has stored therein instructions that, when executed by the processor, produce the topography map by tracking movement of the eye, and time-aligning the tracked eye movement with the detected changes in the spacing or shape of the Purkinje image.

18. The article of manufacture of claim 16 wherein the non-transitory machine-readable medium has stored therein instructions that when executed by the processor produce the topography map by:

a) determining a point on the cornea, based on the detected eye position at the time of a given detected change in the spacing or shape of the Purkinje image;

b) computing curvature at said point based on the given detected change; and repeating a)-b) for a plurality of points on the cornea to produce the topography map for an entire surface of the cornea.

* * * * *